United States Patent [19]
Darouiche

[11] Patent Number: 5,853,745
[45] Date of Patent: Dec. 29, 1998

[54] MEDICAL IMPLANT HAVING A DURABLE, RESILIENT AND EFFECTIVE ANTIMICROBIAL COATING

[75] Inventor: Rabih O. Darouiche, Houston, Tex.

[73] Assignee: Baylor College of Medicine, Houston, Tex.

[21] Appl. No.: 824,596

[22] Filed: Mar. 26, 1997

Related U.S. Application Data

[62] Division of Ser. No. 555,028, Nov. 8, 1995, Pat. No. 5,765,145.

[51] Int. Cl.$^6$ .............................. A61F 2/00; A61F 2/02; A61M 25/00
[52] U.S. Cl. ..................... 424/423; 424/424; 604/265; 623/11
[58] Field of Search ................... 623/1, 3, 4, 9, 623/11, 12, 901; 604/264, 265; 424/423, 424, 405

[56] References Cited

U.S. PATENT DOCUMENTS

| | | | |
|---|---|---|---|
| 4,708,765 | 11/1987 | Newman et al. | 156/626 |
| 4,749,585 | 6/1988 | Greco et al. | 427/2.26 |
| 4,767,411 | 8/1988 | Edmunds | 604/180 |
| 4,894,231 | 1/1990 | Moreau et al. | 427/2.21 |
| 4,976,703 | 12/1990 | Franetzki et al. | 604/247 |
| 5,019,096 | 5/1991 | Fox, Jr. et al. | 623/1 |
| 5,197,977 | 3/1993 | Hoffman, Jr. et al. | 427/2.25 |
| 5,238,749 | 8/1993 | Cueman et al. | 424/409 |
| 5,272,012 | 12/1993 | Opolski | 604/265 |
| 5,290,548 | 3/1994 | Goldberg et al. | 427/595 |
| 5,425,639 | 6/1995 | Anders | 433/169 |
| 5,464,650 | 11/1995 | Berg et al. | 427/2.28 |
| 5,569,463 | 10/1996 | Helmus et al. | 427/2.12 |
| 5,571,567 | 11/1996 | Shah | 427/407.1 |
| 5,599,576 | 2/1997 | Opolski | 427/2.3 |
| 5,609,629 | 3/1997 | Fearnot et al. | 623/1 |
| 5,624,704 | 4/1997 | Darouiche et al. | 427/2.24 |

*Primary Examiner*—Diana Dudash
*Attorney, Agent, or Firm*—Fulbright & Jaworski L.L.P.; Thomas D. Paul, Esq.; Ricardo A. Price, Esq.

[57] ABSTRACT

A medical implant, such as an orthopedic implant, having a first antimicrobial coating layer and a second protective layer, and a method for coating such an implant is provided. The medical implant has one or more of its surfaces coated with an antimicrobial coating layer and a protective coating layer formed over the antimicrobial coating layer. The protective coating layer includes a durable coating layer composed of material such as collodion and nylon, and a resilient coating layer composed of material such as collodion. The coating layers are applied by applying an antimicrobial coating layer to at least a portion of the surfaces of the medical implant, applying a durable coating layer over the antimicrobial coating layer, and applying a resilient coating layer over the durable coating layer.

4 Claims, No Drawings

MEDICAL IMPLANT HAVING A DURABLE, RESILIENT AND EFFECTIVE ANTIMICROBIAL COATING

This is a division of application Ser. No. 08/555,028 filed Nov. 8, 1985, now U.S. Pat. No. 5,765,145.

BACKGROUND OF THE INVENTION

1. Field of the Invention

The present invention relates to indwelling medical devices, such as orthopedic implants, which are coated with a first layer of one or more antimicrobial agents to inhibit the growth of bacterial and fungal organisms, and a second protective layer. The invention also relates to a method of coating the indwelling medical device with a first layer of one or more antimicrobial agents and a second protective layer.

2. Description of the Prior Art

Indwelling orthopedic devices are becoming more prevalent, partly to meet the demands of a growing elderly population. For example, over 4.4 million people in the United States have an indwelling orthopedic device, and over 1.3 million people in the U.S. have an existing joint implant. In the United States alone, 120,000 hip replacement surgeries are performed each year. The benefit derived from these orthopedic and other prosthetic devices is often offset by infectious complications, which can occasionally lead to sepsis and death. The most common organisms causing these infectious complications are Staphylococcus epidermidis and Staphylococcus aureus which account for about two-thirds of cases of infection. Other gram-positive bacteria, gram-negative bacteria and fungal organisms (Candida) account for the remaining one-third of cases.

About 5–20% of fracture fixation devices (pins, nails, screws, etc.) and about 1–3% of orthopedic joint implants become infected. Cure of infected orthopedic implants, such as joint prostheses, usually requires both removal of the prosthesis and administration of a long course of antibiotics. In most cases, this is followed by re-implantation of a new joint prosthesis weeks or months later, after making sure that the infection has been eradicated. This underscores the tremendous medical (major morbidity in most patients and inability to achieve cure in at least 10–20% of infected cases) and economic impact of infectious complications of orthopedic implants. For instance, the estimated cost of removing an infected hip joint prosthesis, administering 4–6 week course of IV antibiotics and re-insertion of a new joint prosthesis varies between $100,000 and $150,000.

A considerable amount of attention and study has been directed toward preventing colonization of bacterial and fungal organisms on the surfaces of orthopedic implants by the use of antimicrobial agents, such as antibiotics, bound to the surface of the materials employed in such devices. The objective of such attempts has been to produce a sufficient bacteriostatic or bactericidal action to prevent colonization.

Various methods have previously been employed to coat the surfaces of medical devices with an antibiotic. For example, one method of coating the devices would be to first apply or absorb to the surface of the medical device a layer of surfactant, such as tridodecylmethyl ammonium chloride (TDMAC) followed by an antibiotic coating layer. For example, a medical device having a polymeric surface, such as polyethylene, silastic elastomers, polytetrafluoroethylene or Dacron, can be soaked in a 5% by weight solution of TDMAC for 30 minutes at room temperature, air dried, and rinsed in water to remove excess TDMAC. The device carrying the absorbed TDMAC surfactant coating can then be incubated in an antibiotic solution for up to one hour or so, allowed to dry, then washed in sterile water to remove unbound antibiotic and stored in a sterile package until ready for implantation. In general, the antibiotic solution is composed of a concentration of 0.01 mg/ml to 60 mg/ml of each antibiotic in an aqueous pH 7.4–7.6 buffered solution, sterile water, or methanol. According to one method, an antibiotic solution of 60 mg of minocycline and 30 mg of rifampin per ml of solution is applied to the TDMAC coated medical device.

A further method known to coat the surface of medical devices with antibiotics involves first coating the selected surfaces with benzalkonium chloride followed by ionic bonding of the antibiotic composition. See, e.g., Solomon, D. D. and Sherertz, R. J., *J. Controlled Release*, 6:343–352 (1987) and U.S. Pat. No. 4,442,133.

Other methods of coating surfaces of medical devices with antibiotics are taught in U.S. Pat. No. 4,895,566 (a medical device substrate carrying a negatively charged group having a pK of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders).

These and many other methods of coating medical devices with antimicrobial agents (antibiotics and/or antiseptics) appear in numerous patents and medical journal articles. Practice of the prior art coating methods results in an orthopedic implant or medical device wherein the effectiveness of the coating diminishes over time. After insertion of the medical device or orthopedic implant, the antibiotics and/or antiseptics quickly leach from the surface of the device into the surrounding environment. Over a relatively short period of time, the amount of antibiotics and/or antiseptics present on the surface decreases to a point where the protection against bacterial and fungal organisms is no longer effective. Furthermore, during implantation of orthopedic fracture fixation devices, such as intramedullary nails and external fixation pins, much of the antimicrobial coating sloughs off due to grating of the coated implant against the bone during insertion of the implant.

Accordingly, there is a need for a durable antimicrobial coated orthopedic implant or medical device that can remain in vivo for extended periods of time without losing its antimicrobial efficacy. There is also a need for a resilient antimicrobial coated orthopedic implant that can be inserted into bone with minimal sloughing of the antimicrobial layer from the surface of the device.

SUMMARY OF THE INVENTION

An object of the present invention is the provision of a durable antimicrobial coated orthopedic device or other medical implant having a durable material layer that decreases the rate of leaching of antimicrobial agents into the surrounding environment.

A further object is the provision of an antimicrobial coated medical implant or orthopedic device having mechanical resiliency to minimize or avoid sloughing of the antimicrobial layer from the device during insertion.

Another object is the provision of a protective coating layer to protect certain photosensitive antimicrobial agents from exposure to light or air.

Yet a further object of the invention is the provision of a smooth and shiny finish to antimicrobial coated orthopedic devices.

A further object of the invention is the provision of a practical, inexpensive, safe and effective method for coating various types of medical implants with an antimicrobial layer covered by a protective layer.

Thus in accomplishing the foregoing objects, there is provided in accordance with one aspect of the present invention a medical implant having one or more of its surfaces coated with a composition comprising an antimicrobial coating layer comprising an antimicrobial agent in an effective concentration to inhibit the growth of bacterial and fungal organisms; and a protective coating layer formed over said antimicrobial coating layer.

According to one aspect of the invention, the antimicrobial composition layer may further comprise a mixture of a polymeric sticking agent and an acid solution.

According to one embodiment, the protective coating layer may comprise a first durable coating layer of material, such as nylon or a mixture of nylon and collodion or nylon and polyvinyl, formed over said antimicrobial coating layer; and a second resilient coating layer of material, such as collodion, formed over said first durable coating layer of material.

According to another embodiment, the protective coating may comprise a first resilient coating layer of material, such as collodion, formed over said antimicrobial coating layer; and a second durable coating layer of material, such as nylon or a mixture of nylon and collodion or nylon and polyvinyl, formed over said first resilient coating layer of material.

The antimicrobial coating layer preferably comprises an antimicrobial solution comprising an antimicrobial agent and a polyvinyl moiety dissolved in an acid solution applied to at least a portion of the surfaces of said medical implant. The antimicrobial agent may preferably be a combination of antibiotics, such as minocycline and rifampin, or a combination of antiseptics, such as chlorhexidine, cetylpyridinium chloride, methylisothiazolone, thymol, α-terpineol and chloroxylenol.

According to a further aspect of the invention, there is provided a method for coating a medical implant comprising the steps of applying, to at least a portion of the surfaces of said medical implant, an antimicrobial coating layer, having an antimicrobial agent in an effective concentration to inhibit the growth of bacterial and fungal organisms; and applying a protective coating layer over said antimicrobial coating layer.

According to one embodiment, the step of applying a protective coating may comprise applying a first durable coating layer of material, such as a mixture of collodion and nylon, over said antimicrobial coating layer; and applying a second resilient coating layer of material, such as collodion, over said first durable coating layer of material.

According to an alternative embodiment, the step of applying a protective coating may comprise applying a first resilient coating layer of material, such as collodion, over said antimicrobial coating layer; and applying a second durable coating layer of material, such as a mixture of nylon and collodion, over said first resilient coating layer of material.

According to a further embodiment of the invention, a method for coating a medical implant is provided comprising the steps of dipping said medical implant into an antimicrobial solution for a period of approximately one minute, said antimicrobial solution comprising a mixture of chlorhexidine, methylisothiazolone and thymol, in effective concentration to inhibit the growth of bacterial and fungal organisms, and polyvinyl butyryl-co-vinyl alcohol co-vinyl acetate dissolved in a 50:50 solution of glacial acetic acid and formic acid; drying the antimicrobial coated medical implant for a period of approximately four hours; dipping the antimicrobial coated medical implant into a 50:50 solution of collodion and nylon for a period of a few seconds; drying the collodion and nylon coated medical implant for a period of approximately two hours; dipping the collodion and nylon coated medical implant into a solution of collodion for a period of a few seconds; and drying the collodion coated medical implant.

Still a further embodiment of the present invention provides a method for coating a medical implant, such as an orthopedic implant, with a combination of antimicrobial agents comprising the steps of dissolving the combination of antimicrobial agents and a polymeric sticking agent in an acid solution to form an antimicrobial solution; and applying said antimicrobial solution, in an effective concentration to inhibit the growth of bacterial and fungal organisms, to at least a portion of the surfaces of said medical implant. The implant also may be allowed to dry after the antimicrobial solution is applied to the surfaces thereof.

DETAILED DESCRIPTION

The term "antimicrobial agent" as used in the present invention means antibiotics, antiseptics, disinfectants and other synthetic moieties, and combinations thereof, that are soluble in organic solvents such as alcohols, ketones, ethers, aldehydes, acetonitrile, acetic acid, formic acid, methylene chloride and chloroform.

Classes of antibiotics that can possibly be used include tetracyclines (i.e. minocycline), rifamycins (i.e. rifampin), macrolides (i.e. erythromycin), penicillins (i.e. nafcillin), cephalosporins (i.e. cefazolin), other beta-lactam antibiotics (i.e. imipenem, aztreonam), aminoglycosides (i.e. gentamicin), chloramphenicol, sufonamides (i.e. sulfamethoxazole), glycopeptides (i.e. vancomycin), quinolones (i.e. ciprofloxacin), fusidic acid, trimethoprim, metronidazole, clindamycin, mupirocin, polyenes (i.e. amphotericin B), azoles (i.e. fluconazole) and beta-lactam inhibitors (i.e. sulbactam).

Examples of specific antibiotics that can be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al., U.S. Pat. No. 4,642,104, herein incorporated by reference, will readily suggest themselves to those of ordinary skill in the art.

Examples of antiseptics and disinfectants are thymol, α-terpineol, methylisothiazolone, cetylpyridinium, chloroxylenol, hexachlorophene, cationic biguanides (i.e. chlorhexidine, cyclohexidine), methylene chloride, iodine and iodophores (i.e. povidone-iodine), triclosan, furan medical preparations (i.e. nitrofurantoin, nitrofurazone), methenamine, aldehydes (glutaraldehyde, formaldehyde)

and alcohols. Other examples of antiseptics and disinfectants will readily suggest themselves to those of ordinary skill in the art.

Minocycline is a semisynthetic antibiotic derived from tetracycline. It is primarily bacteriostatic and exerts its antimicrobial effect by inhibiting protein synthesis. Minocycline is commercially available as the hydrochloride salt which occurs as a yellow, crystalline powder and is soluble in water and slightly soluble in organic solvents including alcohols, ketones, ethers, aldehydes, acetonitrile, acetic acid, methylene chloride and chloroform. Minocycline is active against a wide range of gram-negative and gram-positive organisms.

Rifampin is a semisynthetic derivative of rifamycin B, a macrocyclic antibiotic compound produced by the mold Streptomyces mediterranic. Rifampin inhibits bacterial DNA-dependent RNA polymerase activity and is bactericidal in nature. Rifampin is commercially available as a red-brown crystalline powder and is very slightly soluble in water and freely soluble in acetic aqueous solutions and organic solutions including alcohols, ketones, ethers, aldehydes, acetonitrile, acetic acid, methylene chloride and chloroform. Rifampin possesses a broad spectrum activity against a wide range of gram-positive and gram-negative bacteria.

Erythromycin is a macrolide antibiotic produced by a strain of Streptomyces erythreaus. Erythromycin exerts its antibacterial action by inhibition of protein synthesis without affecting nucleic acid synthesis. It is commercially available as a white to off-white crystal or powder slightly soluble in water and soluble in organic solutions including alcohols, ketones, ethers, aldehydes, acetonitrile, acetic acid, methylene chloride and chloroform. Erythromycin is active against a variety of gram-positive and gram-negative bacteria.

Nafcillin is a semisynthetic penicillin that is effective against both penicillin-G-sensitive and penicillin-G-resistant strains of Staphylococcus aureus as well as against pneumococcus, beta-hemolytic streptococcus, and alpha streptococcus (viridans streptococci). Nafcillin is readily soluble in both water and organic solutions including alcohols, ketones, ethers, aldehydes, acetonitrile, acetic acid, methylene chloride and chloroform.

Hexachlorophene is a bacteriostatic antiseptic cleansing agent that is active against staphylococci and other gram-positive bacteria. Hexachlorophene is soluble in both water and organic solutions including alcohols, ketones, ethers, aldehydes, acetonitrile, acetic acid, methylene chloride and chloroform.

Chlorhexidine (Chlorhexidine gluconate) is a biguanide with a very rapid bactericidal activity against a broad range of microorganisms, including gram-positive bacteria (such as staphylococci, Enterococcus species), gram-negative bacteria (such as *Escherichia coli* and *Pseudomonas aeruginosa*) and Candida species. Chlorhexidine causes disruption of microbial cell membranes and precipitation of cellular contents, and its effectiveness is not affected by the presence of organic matter, such as blood. An important attribute of chlorhexidine is its prolonged persistence on the skin, which is beneficial for reducing infections related to medical devices that are usually caused by organisms migrating from skin, such as orthopedic device-related infections. Chlorhexidine is soluble in acetic acid and formic acid, but is generally not soluble in organic solvents. Chlorhexidine has been used extensively as a skin cleanser for over 20 years, and also has been used to coat vascular catheters either alone or in combination with silver sulfadiazine.

Methylisothiazolone (2-Methylisothiazolone Hydrochloride) is a bacteriostatic antiseptic with a broad spectrum antimicrobial activity against gram-positive bacteria (MIC for Staphylococcus aureus=80 μg/ml; MIC for Enterococcus species=80 μg/ml), gram-negative bacteria (MIC for *Escherichia coli*=40 μg/ml; MIC for *Pseudomonas aeruginosa*=80 μg/ml) and Candida species (MIC for Candida albicans=320 μg/ml). Methylisothiazolone is soluble in formic acid and organic solvents, but is not soluble in acetic acid. Methylisothiazolone has been used to prevent bacterial and algae growth in water cooling systems.

Thymol(5-methyl-2 isopropyl phenol) is a bacteriostatic antiseptic with a broad spectrum antimicrobial activity against gram-positive bacteria (such as staphylococci and Enterococcus species), gram-negative bacteria (such as *Escherichia coli* and *Pseudomonas aeruginosa*) and Candida species. Thymol is soluble in acetic acid and organic solvents, but is not soluble in formic acid. Thymol has been used in mouth wash preparations.

α-Terpineol (α-α-4-trimethyl-3-cyclohexine-1-methanol) is a bacteriostatic antiseptic that is chemically related to thymol and shares with thymol the same broad spectrum antimicrobial activity against gram-positive bacteria (such as staphylococci and Enterococcus species), gram-negative bacteria (such as *Escherichia coli* and *Pseudomonas aeruginosa*) and Candida species. α-Terpineol is soluble in acetic acid and organic solvents, but is not soluble in formic acid. α-terpineol has been used in mouth wash preparations.

Cetylpyridinium Chloride (1-Hexadecylpridinium chloride) is an antiseptic which has activity against gram-positive bacteria and Candida. It has been used in mouth lozenges (as in "Cepacol") and in antiseptic creme, tincture, and solution preparations (as in "Fungoid").

Chloroxylenol (4-chloro, 3,5-dimethyl phenol) is an antiseptic which has shown good antimicrobial activity against gram-positive bacteria and fungi, and fair activity against gram-negative bacteria. It has been used in antimicrobial soap solution (as in "Ultradex"), antiseptic creme, tincture and solution preparations (as in "Fungoid"). Its effectiveness is minimally affected by organic matter, and it persists in skin for a few hours.

These antimicrobial agents can be used alone or in combination of two or more of them to obtain a synergistic effect. They are dispersed along the surface of the medical device. One example of an antibiotic combination is a mixture of minocycline and rifampin. This mixture provides a broad spectrum of activity against organisms that cause orthopedic implant related infections, including Staphylococcus epidermidis, Staphylococcus aureus, streptococci, corynebacteria, gram-negative bacilli, and Candida.

Some examples of combinations of antiseptics include a mixture of methylisothiazolone and thymol; chlorhexidine, methylisothiazolone and α-terpineol; thymol and chloroxylenol; chlorhexidine and chloroxylenol; chlorhexidine and cetylpyridinium chloride; or chlorhexidine, methylisothiazolone and thymol. These combinations provide a broad spectrum of activity against a wide variety of organisms. Further, combinations of antiseptics and antibiotics can be used.

The amount of each antimicrobial agent used to coat the medical device varies to some extent, but is at least a sufficient amount to form an effective concentration to inhibit the growth of bacterial and fungal organisms, such as staphylococci, gram-positive bacteria, gram-negative bacilli and Candida.

The term "effective concentration" means that a sufficient amount of the antimicrobial agent is added to decrease, prevent or inhibit the growth of bacterial and/or fungal organisms. The amount will vary for each compound and upon known factors such as pharmaceutical characteristics; the type of medical device; age, sex, health and weight of the recipient; and the use and length of use. It is within the skilled artisan's ability to relatively easily determine an effective concentration for each compound.

The term "sticking agent" as used in the present invention means any of a group of polymeric materials that can be used to coat the surface of a medical implant. Examples of such polymeric materials are "polyvinyl" (as defined below), "collodion" (as defined below) polycarboxylic acids (i.e. polyacrylic acid, polymethacrylic acid, polymaleic acid, poly-(maleic acid monoester), polyaspartic acid, polyglutamic acid, aginic acid or pectimic acid), polycarboxylic acid anhydrides (i.e. polymaleic anhydride, polymethacrylic anhydride or polyacrylic acid anhydride), polyamines, polyamine ions (i.e. polyethylene imine, polyvinylamine, polylysine, poly-(dialkylamineoethyl methacrylate), poly-(dialkylaminomethyl styrene) or poly-(vinylpyridine)), polyammonium ions (i.e. poly-(2-methacryloxyethyl trialkyl ammonium ion), poly-(vinylbenzyl trialkyl ammonium ion), poly-(N,N,-alkylpyridinium ion) or poly-(dialkyloctamethylene ammonium ion) and polysulfonates (i.e. poly-(vinyl sulfonate) or poly-(styrene sulfonate)). Linear copolymers, crosslinked copolymers, graft polymers and block copolymers containing the monomers as constituents of the above exemplified polymers can also be used. These and other useful polymeric materials are listed in Sakamoto et al., U.S. Pat. No. 4,642,104, and are herein incorporated by reference.

The term "polyvinyl" as used in the present invention means any of a group of polymerized vinyl compounds such as PV-coA-coA (Polyvinyl butyryl-co-vinyl alcohol-co-vinylacetate), PV-coA-coA plus hydroxylapatite, PVP (Polyvinyl pyrrolidone), PVP-coVA (Polyvinyl pyrrolidone co-vinyl acetate dissolved in 2-propanol) and combinations thereof.

The term "nylon" as used in the present invention means any of a group of synthetic long-chain polymeric amides with recurring amide groups having great strength and elasticity, such as polycaprolactam, polylauryl-lactam and polyhexamethylene sebacamide.

The term "collodion" as used in the present invention means any of a group of. colorless or pale-yellow, viscous solutions of pyroxylin or nitrocellulose in a mixture of alcohol and ether, which dries quickly and forms a tough, elastic film.

The term "bacterial and fungal organisms" as used in the present invention means all genuses and species of bacteria and fungi, including but not limited to all spherical, rod-shaped and spiral organisms. One skilled in the art recognizes that a variety of source books which list and describe bacteria and fungi are available, for example in the textbook "Principles and Practice of Infectious Diseases", Mandell et al., 4th edition, 1995, Churchill Livingstone, N.Y. Some examples of bacteria are staphylococci (i.e. *Staphylococcus epidermidis, Staphylococcus aureus), Enterococcus faecalis, Pseudomonas aeruginosa, Escherichia coli*, other gram-positive bacteria and gram-negative bacili. One example of a fungus is Candida albicans.

The term "medical implant" means medical devices which are indwelling or implanted in humans. These can be either permanent or temporary. The medical devices that are amenable to coating by the antimicrobial combinations are generally composed of metallic material. Examples of metallic materials that can be coated by the method of the present invention are metallic alloys, such as stainless steel, titanium, tivanium, vitallium, chromium alloy, cobalt alloy and the like.

Particular metallic devices especially suited for application of the antimicrobial combinations of this invention include orthopedic implants such as joint prostheses, screws, nails, nuts, bolts, plates, rods, pins, wires, inserters, osteoports, halo systems and other orthopedic devices used for stabilization or fixation of spinal and long bone fractures or disarticulations. Other metallic devices may include non-orthopedic devices such as tracheostomy devices, intraurethral and other genitourinary implants, stylets, dilators, stints, wire guides and access ports of subcutaneously implanted vascular catheters.

In addition to antimicrobial coating of metallic medical implants, the method of coating described in this invention, or a modification thereof, can be potentially used to incorporate antimicrobial agents onto coating compounds that are applied over miscellaneous surfaces, such as hospital floors, nursing counters, counters adjacent to washing basins, desks, etc. to decrease transmission of hospital antibiotic resistant microbial flora, such as methicillin resistant staphylococcus aureris, vancomycin-resistant enterococci and antibiotic-resistant gram-negative bacteria on the skin of healthcare personnel and patients. Another potential application would be the antimicrobial coating of kitchen counters to decrease transmission of organisms that cause food-borne poisoning, such as Salmonella species and *Escherichia coli*.

The present invention is directed to a medical implant having an antimicrobial layer and a protective layer, and a method for coating such an implant with an antimicrobial layer and a protective layer. The protective layer slows the leaching of antimicrobial agents from the surface of the implant and is resilient to resist sloughing of the antimicrobial agents during implantation. Further, the protective layer can also protect certain photosensitive antimicrobial agents from exposure to light or air. For instance, some antimicrobial agents, such as methylisothiazolone, are regarded as photosensitive. Moreover, when orthopedic devices coated with a single layer of PV-coVA-co-VA mixed with minocycline and rifampin were exposed to air for few days, the coating layer became dry, got darker in color, and became much more likely to slough off the device upon scratching.

One embodiment of the present invention is a medical implant having one or more of its surfaces coated with an antimicrobial coating layer having an antimicrobial agent in an effective concentration to inhibit the growth of bacterial and fungal organisms, and a protective coating layer formed over said antimicrobial coating layer.

The antimicrobial coating layer is applied to at least a portion of the surfaces of said medical implant and preferably is comprised of an antimicrobial solution having an antimicrobial agent and a polyvinyl, preferably polyvinyl butyryl-co-vinyl alcohol co-vinyl acetate, dissolved in an acid solution. According to one preferred aspect, the antimicrobial agent is selected from an antibiotic, antiseptic, disinfectant or a combination thereof. The combination can be within a group such as antibiotics, like minocycline and rifampin, or an antiseptic like chlorhexidine, methylisothiazolone and thymol; chlorhexidine, α-terpineol and methylisothiazolone; thymol and chloroxylenol; thymol and methylisothiazolone; chlorhexidine and chloroxylenol; or chlorhexidine and cetylpyridium chloride. Further the combination could be a mixture of groups such as an antibiotic and an antiseptic or a disinfectant.

In order to properly form the antimicrobial solution, the antimicrobial agent and the polyvinyl must be soluble in the acid solution. Therefore, where the combination of chlorhexidine, methylisothiazolone and thymol is used, a 50:50 solution of glacial acetic acid and formic acid is required to fully dissolve all three antiseptics.

According to another embodiment of the invention, the antimicrobial solution comprises a mixture of a combination of antimicrobial agents, a polymeric sticking agent and an acid solution. The preferred antimicrobial solution according to this embodiment comprises a mixture of chlorhexidine and chloroxylenol. The polymeric sticking agent is preferably polyvinyl butyryl-co-vinyl alcohol co-vinyl acetate, and the acid solution is a mixture of glacial acetic acid and formic acid.

The medical implant according to this embodiment is formed by applying an antimicrobial solution, in an effective concentration to inhibit the growth of bacterial and fungal organisms, to at least a portion of the surfaces of the medical implant. The implant also may be allowed to dry after the antimicrobial solution is applied to the surfaces thereof. The antimicrobial solution is formed by dissolving a combination antimicrobial agents, and a polymeric sticking agent in an acid solution to form an antimicrobial solution. Preferably a mixture of chlorhexidine, methylisothiazolone and α-terpineol, and polyvinyl butyryl-co-vinyl alcohol co-vinyl acetate are dissolved in a solution of formic acid and glacial acetic acid to form the antimicrobial solution.

According to one preferred method, the step of applying the antimicrobial solution comprises dipping the device into the antimicrobial solution for a period of approximately one minute; and the step of drying the device for at least about 4 hours.

In one aspect of the present invention the protective coating layer can be a single layer. It is either a durable coating layer or a resilient coating layer. In the preferred embodiment the protective coating layer is at least two layers and includes a durable coating layer and a resilient coating layer.

According to another aspect of the present invention, the protective coating layer is preferably comprised of a durable coating layer, such as a mixture of collodion and nylon and a resilient coating layer such as collodion. The nylon is preferably selected from the group consisting of polycaprolactam, polylauryl-lactam and polyhexamethylene sebacamide. The order of the protective layers can be either with the resilient layer coating the antimicrobial layer and the durable layer coating the resilient layer or the reverse, i.e., the durable layer coating the antimicrobial layer and the resilient layer coating the durable layer.

According to a further embodiment of the invention, there is provided a method for coating a medical implant comprising the steps of applying an antimicrobial coating layer to at least a portion of the surfaces of said medical implant comprising an antimicrobial agent in an effective concentration to inhibit the growth of bacterial and fungal organisms; and applying a protective coating layer over said antimicrobial coating layer.

According to one aspect, the step of applying an antimicrobial coating layer to at least a portion of the surfaces of the medical implant comprises applying an antimicrobial solution comprised of an antimicrobial agent and a polyvinyl. Preferably the polyvinyl is polyvinyl butyryl-co-vinyl alcohol co-vinyl acetate, dissolved in an acid solution. The antimicrobial agent may comprise an antibiotic, an antiseptic, a disinfectant or a combination thereof.

According to one preferred embodiment, the antimicrobial coating layer is applied by dipping the medical implant into the antimicrobial solution for a period of approximately one minute. The antimicrobial coated implant may then be allowed to dry for a period of approximately four hours prior to application of the protective coating.

The step of applying a protective coating comprises applying a durable coating layer, and applying a resilient coating layer. The durable coating layer and resilient coating layer can be applied in either order. For example, the durable coating layer could be applied over the antimicrobial layer and then the resilient layer applied over the durable coating layer or the reverse, the resilient coating layer is applied over the antimicrobial layer and then the durable coating layer is applied over the resilient coating layer.

According to one embodiment, the durable coating layer is applied by dipping the antimicrobial coated medical implant into a 50:50 solution of collodion and nylon for a period of a few seconds (approximately 5–10 seconds). The collodion and nylon coated medical implant is then allowed to dry for a period of approximately two hours. The resilient coating layer is then applied by dipping the collodion and nylon coated medical implant into a solution of collodion for a period of a few seconds (approximately 5–10 seconds). It can then be allowed to dry for at least about two hours.

According to a further embodiment of the invention, a method for coating a medical implant is provided comprising the steps of dipping said medical implant into an antimicrobial solution for a period of approximately one minute, said antimicrobial solution comprising a mixture of chlorhexidine, methylisothiazolone and thymol, in effective concentration to inhibit the growth of bacterial and fungal organisms, and polyvinyl butyryl-co-vinyl alcohol co-vinyl acetate dissolved in a 50:50 solution of glacial acetic acid and formic acid; drying the antimicrobial coated medical implant for a period of approximately four hours; dipping the antimicrobial coated medical implant into a 50:50 solution of collodion and nylon for a period of a few seconds (approximately 5–10 seconds); drying the collodion and nylon coated medical implant for a period of approximately two hours; dipping the collodion and nylon coated medical implant into a solution of collodion for a period of a few seconds (approximately 5–10 seconds); and drying the collodion coated medical implant.

In other embodiments of the invention the antimicrobial agents are added to either or both the durable layer or the resilient layer.

The following examples are offered by way of illustration and are not intended to limit the invention in any manner.

EXAMPLE 1

TRIPLE LAYER COATING VERSUS SINGLE LAYER COATING OF ORTHOPEDIC DEVICE

A single layer coating of antimicrobial material was applied to a first group of 0.5×2" stainless steel cylinders (diameter 12 mm) by dipping the cylinders into an acid solution (50:50 glacial acetic acid and formic acid) that has polyvinyl butyryl-co-vinyl alcohol-co-vinyl acetate (PV-coVA-coVA; 85 mg/ml) mixed with an antiseptic combination of chlorhexidine (120 mg/ml), methylisothiazolone (60 mg/ml) and thymol (20 mg/ml) for 1 minute at 50° C. Cylinders were then allowed to dry for at least four hours.

A triple layer coating of material was applied to a second group of 0.5×2" stainless steel cylinders (diameter 12 mm) by first dipping each cylinder into an acid solution (50:50 glacial acetic acid and formic acid) that has polyvinyl butyryl-co-vinyl alcohol-co-vinyl acetate (PV-coVA-coVA; 85 mg/ml) mixed with an antiseptic combination of chlorhexidine (120 mg/ml), methylisothiazolone (60 mg/ml) and thymol (20 mg/ml) for 1 minute at 50° C. The cylinders were then allowed to dry for 4 hours, and dipped for just a few seconds in 50:50 solution of collodion plus nylon (final concentration of polycaprolactam is 50 mg/ml) at room temperature. After allowing the cylinders to dry for 2 hours, each cylinder was dipped for just a few seconds in collodion at room temperature. The triple layer coated cylinders were allowed to dry for at least 2 hours.

Selected single layer and triple layer coated cylinders were then placed on agar plates that had been freshly overlaid with one of the microorganisms shown below in Table 1. After 18–24 hours of incubation in the agar plates at 37° C., the zones of inhibition measurements shown in Table 1 were taken. The amount of chlorhexidine adherent to selected single layer and triple layer coated cylinders was determined by high-performance liquid chromatography (HPLC).

TABLE 1

| Coating | Zones of inhibition (m.m.) | | | HPLC |
| --- | --- | --- | --- | --- |
| | Staph. epidermidis | Pseud. aeruginosa | Candida albicans | Chlorhexidine mg/device |
| Single layer | 52 | 44 | 43 | 26.182 |
| Triple layer | 47 | 40 | 41 | 20.195 |

The results demonstrate that the triple layer coating does not significantly decrease the antimicrobial activity or the overall amount of antimicrobial agents adherent to the surface of the cylinders. The results further show that the initial antimicrobial efficacy of the triple layer coating is not significantly different from the initial efficacy of the single layer coating.

EXAMPLE 2

TRIPLE LAYER COATING VERSUS SINGLE LAYER COATING OVER TIME

Some of the single layer and triple layer coated cylinders of Example 1 were allowed to dry overnight and were then placed in human serum at 37° C. for 3 days or 2 weeks. The coated cylinders were then removed from the serum and placed on agar plates that had been freshly overlaid with one of the microorganisms shown below in Table 2. After 18–24 hours of incubation at 37° C., the zones of inhibition measurements shown in Table 2 were taken.

TABLE 2

| | | Zones of inhibition (m.m.) | | |
| --- | --- | --- | --- | --- |
| Coating | Time | Staph. epidermidis | Pseud. aeruginosa | Candida albicans |
| Single layer | Initial | 52 | 44 | 43 |
| Single layer | 3 days | 27 | 25 | 23 |
| Single layer | 2 weeks | 16 | 0 | 0 |
| Triple layer | Initial | 47 | 40 | 41 |
| Triple layer | 2 weeks | 21 | 21 | 22 |

These results show that triple layer coating provides more durable, long lasting efficacy than the single layer coating. The zones of inhibition are reduced by about 50% of the initial zone of inhibition after only 3 days of incubating the single layer coating in human serum and cease to exist after two weeks for Candida and Pseudomonas, whereas the triple layer coating shows zones of inhibition reduced by about 50% of the initial zone of inhibition after 2 weeks while incubated in human serum.

EXAMPLE 3

SINGLE VS TRIPLE LAYER OF ANTIBIOTIC COATING

A single layer coating of antimicrobial material was applied to the first group of 0.5×2" stainless steel devices by dipping the devices into a solution of glacial acetic acid that has minocycline (50 mg/ml) and rifampin (50 mg/ml) and PV-coVA-coVA (70 mg/ml) for one minute at 50° C.

A triple layer coating material was applied to the second group of devices over the first coating layer using procedures that were very similar to those described in Example 1. Selected devices that had been coated with single layer and with triple layers were incubated in human serum for three weeks at 37° C.

TABLE 3

| | Zones of inhibition (m.m.) | | | |
| --- | --- | --- | --- | --- |
| Coating Method | Initial | 1 week | 2 week | 3 week |
| 1 layer | 45 | 43 | 37 | 32 |
| 3 layers | 40 | 43 | N/A | 41 |

The results demonstrate that the antimicrobial efficacy of the triple layer coating does not decrease significantly over time, whereas there is a decrease in the zones of inhibition provided by the single layer coating. This clearly shows a fairly long lasting antimicrobial efficacy of the triple layer versus the single layer coating with antibiotics.

EXAMPLE 4

RATES OF LEACHING OF ANTIBIOTICS FROM COATED ORTHOPEDIC DEVICES

The leaching of antibiotics from orthopedic devices (0.5× 2" stainless steel cylinders with diameter 12 mm) with various coating layers were tested. In this procedure coating method A involved a single layer coating with minocycline (50 mg/ml) and rifampin (50 mg/ml) in a similar fashion to the layer formed in Example 3. Coating method B was similar to coating method A but involved dipping in a 40:60 mixture of the solution in A with collodion. Coating method C referred to a two layer coating in which the first layer was the same as in A and the second layer was a 50:50 nylon::collodion (final concentration of polycaprolactam=25 mg/ml). The coating method D involved a two layer coating in which the first layer was prepared as described in coating method A and a second layer was strictly a layer of collodion. Coating method E referred to a triple layer coating in which the first layer was the same as in coating method A, the second layer was a layer of 50:50 nylon:collodion (final concentration of polycaprolactam 25 mg/ml) and the third layer was of collodion. The layers were formed by the same procedures described in Example 1. Selected orthopedic devices were incubated in human serum at 37° C. for one week. The amounts of antibiotics bound to devices before and after incubation in serum were determined by HPLC. The percentage residual amounts of antibiotics that were still bonded to coated devices after one week incubation in serum are compared below.

TABLE 4

| | % residual after 1 week | |
|---|---|---|
| Coating Method | Minocycline | Rifampin |
| A | 10.1% | 4.9% |
| B | 11.5% | 16.7% |
| C | 43.5% | 53.7% |
| D | 66% | 62.5% |
| E | 76.6% | 74.1% |

The experiment clearly shows that the triple layer coating method (method E) was the most effective in decreasing the leaching of antibiotics while incubating orthopedic devices in serum at 37° C. These results indicate that there was longer durability of antimicrobial activity in multiple coated devices. The mere combination of polyvinyl compound and collodion in a single-layer coating solution (method B) did not significantly improve the durability of coated devices, and only when these compounds were incorporated into different layers of coating (methods C, D and E) was there a remarkable increase in durability.

EXAMPLE 5

ANTISEPTIC VS ANTIBIOTIC COATED DEVICES (TRIPLE LAYER)

The effect of antiseptic versus antibiotic coated devices were compared using triple layer devices. In this procedure the antibiotic combination was minocycline (50 mg/ml) and rifampin (50 mg/ml) and the antiseptics were chlorhexidine (120 mg/ml), methylisothiazolone (60 mg/ml) and thymol (20 mg/ml). These coating solutions were prepared and the orthopedic devices were coated and tested as described in Examples 1 and 3. The results are shown below.

TABLE 5

| | Zones of inhibition (m.m.) | | | | | |
|---|---|---|---|---|---|---|
| | S. epidermidis | | P. aerug | | Candida albicans | |
| Coating | Initial | 1 week | Initial | 1 week | Initial | 1 week |
| Antiseptic | 47 | 30 | 40 | 22 | 41 | 24 |
| Antibiotics | 40 | 38 | 18 | 0 | 18 | 0 |

It can be seen that different organisms respond to antiseptics and antibiotics differently. The antiseptic coated orthopedic devices provide rather comparable activity against staphylococci but much better and more lasting activity against gram-negative bacteria and fungi. This reduces potential concerns for developing superinfection of antibiotic-coated devices with organisms other than staphylococci and abolishes concerns for development of antibiotic resistance when using long-term antibiotic coated devices.

EXAMPLE 6

PERSISTENCE OF ANTIMICROBIAL ACTIVITY

The persistence of antimicrobial activity was tested using 0.5×2" stainless steel cylinders coated with the antiseptic combination of chlorhexidine (90 mg/ml), methylisothiaz- olone (80 mg/ml) and thymol (20 mg/ml). In the antimicrobial coated layer the antiseptics plus 70 mg/ml of PV were dissolved in a 50:50 solution of glacial acetic acid and formic acid. The devices and coating solutions were preheated to 60° C. The devices were dipped in the coating solution for one minute. The devices were then dried for approximately four hours.

After the four hour drying period the durable coating layer was applied over the antiseptic coating layer. To form a second layer the devices were dipped for few seconds in a 50:50 solution of collodion and nylon (polycaprolactam final concentration of 25 mg/ml) at room temperature. The devices were then allowed to dry for approximately two hours.

The resilient coating layer was then formed by dipping the devices for few seconds in a collodion solution at room temperature. Devices were then allowed to dry for an additional two hours. Devices were then incubated in serum (that was changed every week) at 37° C. for 6.5 weeks and residual zones of inhibition were determined.

TABLE 6

| | Zones of Inhibition m.m. | |
|---|---|---|
| Time | S. aureus Newman strain | S. aureus #2143 |
| 6.5 weeks | 18 | 17 |

These results clearly show that the triple layer provides significant protection against the degradation of the antiseptic activity on the coated devices over a 6.5 week period even in the presence of serum.

EXAMPLE 7

SYNERGY OF ANTISEPTIC (CHLORHEXIDINE PLUS CHLOROXYLENOL) COATED ORTHOPEDIC DEVICES (TRIPLE LAYER)

Synergistic effects of antiseptics were also tested with orthopedic devices that were coated with antiseptics using the triple Layer method. In this method orthopedic devices (0.5×2" stainless steel cylinders) were coated with an individual antiseptic (chlorhexidine 150 mg/ml and chloroxylenol 150 mg/ml) or with the combination of the two antiseptics. The orthopedic devices were coated in the following manner: an antimicrobial coated layer of each antiseptic or the combination of antiseptics was applied by dipping the devices for one minute in a 50:50 solution of formic acid and glacial acetic acid that contains the antiseptic(s) and PV-coA-coA (85 mg/ml). The devices and coating solution were preheated to 45° C. After coating the devices were allowed to dry for about four hours. The durable coated layer was then applied by dipping the antiseptic coated devices for approximately 5–10 seconds in a 50:50 solution of collodion and nylon (25 mg/ml of polycaprolactam as a final concentration). The devices were then allowed to dry for an additional two hours. The resilient coated layer was applied over the durable coated layer by dipping the devices for approximately 5–10 seconds in a collodion solution. The devices were then allowed to dry for an additional two hours. Selected coated devices were then incubated in human serum at 37° C. for one and three weeks. The results of zones of inhibition are shown below.

TABLE 7

| Coating | Zones of inhibition (m.m.) | | | | | | | | |
|---|---|---|---|---|---|---|---|---|---|
| | S. epidermidis | | | P. aerug | | | Candida albicans | | |
| | Init. | 1 wk | 3 wk | Init. | 1 wk | 3 wk | Init. | 1 wk | 3 wk |
| Chlorhexidine | 22 | N/A | N/A | 20 | N/A | N/A | 26 | N/A | N/A |
| Chloroxylenol | 32 | N/A | N/A | 13 | N/A | N/A | 28 | N/A | N/A |
| Combination | 35 | 30 | 28 | 21 | 20 | 18 | 41 | 35 | 34 |

The results clearly show that the coating of orthopedic devices with the combination of chlorhexidine and chloroxylenol provides synergistic activity, particularly against Candida. This reduces potential concerns for developing fungal superinfection of coated devices. Even after 1–3 weeks of incubation in serum at 37° C., the devices coated with the combination of chlorhexidine and chloroxylenol continue to provide significant broad spectrum antimicrobial activity. These results are in agreement with HPLC measurements of levels of the antiseptic agents bonded to coated devices. For instance, the residual amounts of chlorhexidine and chloroxylenol on antiseptic-coated devices that had been incubated in serum for one week were 44.9% and 46.1%, respectively, when compared to amounts of antiseptics on devices prior to incubation in serum.

EXAMPLE 8

ANTIMICROBIAL ACTIVITY OF SURFACES COATED WITH THE COMBINATION OF CHLORHEXIDINE AND CETYLPYRIDINIUM CHLORIDE (TRIPLE LAYER)

In this example, 0.5×2" stainless steel devices were coated with the antiseptic combination of chlorhexidine (150 mg/ml) and cetylpyridinium chloride (50 mg/ml) using the triple layer coating method.

The first layer comprised antiseptics plus PV-coA-coA 85 mg/ml dissolved in a 50:50 solution of glacial acetic acid and formic acid. The devices were dipped in coating solution for one minute at 50° C. The devices were dried for 4 hours.

To form the second layer the devices were dipped for few seconds in a 50:50 solution of collodion and nylon (polycaprolactam; final concentration of nylon=25 mg/ml) at room temperature. The devices were dried for 2 hours.

The third layer was formed by dipping devices in a collodion solution at room temperature. The devices were dried for at least 2 hours. The results are shown in Table 8.

TABLE 8

| Zones of Inhibition (m.m.) | | |
|---|---|---|
| S. aureus | Pseudomonas aeruginosa | Salmonella species |
| 25 | 18 | 16 |

The zone of inhibition results show that there is a broad range of antimicrobial activity provided to surfaces coated with the combination of chlorhexidine and cetylpyridinium chloride. The spectrum of antimicrobial activity includes organisms that can be transmitted via contact with surfaces in hospitals (*Staphylococcus aureus* and *Pseudomonas aeruginosa*) and in the kitchen (*Salmonella* species).

EXAMPLE 9

ANTIMICROBIAL ACTIVITY OF METALLIC TRACHEOSTOMY DEVICE COATED WITH THE COMBINATION OF CHLORHEXIDINE AND CHLOROXYLENOL (TRIPLE LAYER)

The inner cannula (diameter 9 mm) of stainless steel tracheostomy devices was coated with the antiseptic combination of chlorhexidine (150 mg/ml) and chloroxylenol (150 mg/ml) using the triple layer coating method:

The first layer contains antiseptics plus PV-coA-coA 85 mg/ml dissolved in a 50:50 solution of glacial acetic acid and formic acid. The devices were dipped in coating solution for one minute at 50°, and dried for 4 hours.

The second layer was formed by dipping devices for about 5–10 seconds in a 50:50 solution of collodion and nylon (polycaprolactam; final concentration of nylon=25 mg/ml) at room temperature, and dipping the devices for 2 hours.

The third layer was formed by dipping devices for about 5–10 seconds in collodion solution at room temperature, and allowing the devices to dry for at least 2 hours.

TABLE 9

| Zones of Inhibition (m.m.) | | |
|---|---|---|
| Methicillin Resistant S. Aureus | Methicillin Sensitive S. aureus | Pseudomonas aeruginosa |
| 30 | 26 | 17 |

The zones of inhibition results demonstrate that there is a broad range of antimicrobial activity provided to tracheostomy devices coated with the combination of chlorhexidine and chloroxylenol. The spectrum of antimicrobial activity includes some of the most common causes of tracheal device-related infection, such as *Staphylococcus aureus* (including methicillin resistant) and *Pseudomonas aeruginosa*.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

The present invention, therefore, is well adapted to carry out the objects and attain the ends and advantages mentioned as well as others inherent therein. While presently preferred embodiments of the invention are given for the purpose of disclosure, numerous changes in the details will readily suggest themselves to those skilled in the art and which are encompassed within the spirit of the invention and the scope of the appended claims.

What I claim is:

1. A medical implant having at least one of its surfaces coated with a composition comprised of:
   an antimicrobial coating layer having an antimicrobial agent in an effective concentration to inhibit the growth of bacterial and fungal organisms relative to uncoated medical implant; and
   a protective coating formed over said antimicrobial coating layer, wherein said protective coating is comprised of:

a durable coating layer; and
a resilient coating layer; and
wherein said resilient coating layer is comprised of collodion.

2. A medical implant having at least one of its surfaces coated with a composition comprised of:
an antimicrobial coating layer having an antimicrobial agent in an effective concentration to inhibit the growth of bacterial and fungal organisms relative to uncoated medical implant; and
a protective coating formed over said antimicrobial coating layer, wherein said protective coating is comprised of:
a durable coating layer; and
a resilient coating layer; and wherein said durable coating layer is comprised of a mixture of collodion and nylon, and said material of said resilient coating layer is comprised of collodion.

3. A medical implant having at least one of its surfaces coated with a composition comprised of:
an antimicrobial coating layer having an antimicrobial agent in an effective concentration to inhibit the growth of bacterial and fungal organisms relative to uncoated medical implant; and further wherein said antimicrobial coating layer coats at least one surface of said medical implant, wherein the antimicrobial coating layer includes polyvinyl butyryl-co-vinyl alcohol co-vinyl acetate dissolved in a 50:50 solution of glacial acetic acid and formic acid and a mixture of antimicrobial compounds selected from the group of mixtures consisting of minocycline and rifampin; chlorhexidine, methylisothiazolone and thymol; chlorhexidine, α-terpineol and methylisothiazolone; thymol and chloroxylenol; methylisothiazolone and thymol; chlorhexidine and chloroxylenol; and chlorhexidine and cetylpyridinium chloride, and wherein the compounds in said mixture are in an effective concentration to inhibit the growth of bacterial and fungal organisms relative to uncoated medical implant;
a protective coating formed over said antimicrobial coating layer;
a durable coating layer selected from the group consisting of nylon, a mixture of collodion and nylon, and a mixture of polyvinyl and nylon covering said antimicrobial coating layer; and
a resilient coating layer of collodion covering said durable coating layer.

4. A medical implant having at least one of its surfaces coated with a composition comprised of:
an antimicrobial coating layer having an antimicrobial agent in an effective concentration to inhibit the growth of bacterial and fungal organisms relative to uncoated medical implant; wherein said antimicrobial coating layer coats at least one surface of said medical implant, wherein the antimicrobial coating layer includes polyvinyl butyryl-co-vinyl alcohol co-vinyl acetate dissolved in glacial acetic acid or a 50:50 solution of glacial acetic acid and formic acid and a mixture of antimicrobial compounds selected from the group of mixtures consisting of minocycline and rifampin; chlorhexidine, methylisothiazolone and thymol; chlorhexidine, α-terpineol and methylisothiazolone; thymol and chloroxylenol; methylisothiazolone and thymol; chlorhexidine and chloroxylenol; and chlorhexidine and cetylpyridinium chloride, wherein the compounds in said mixture are in an effective concentration to inhibit the growth of bacterial and fungal organisms relative to uncoated medical implant;
a protective coating formed over said antimicrobial coating layer;
a resilient coating layer of collodion covering said antimicrobial coating layer; and
a durable coating layer selected from the group consisting of nylon, a mixture of collodion and nylon, and a mixture of polyvinyl and nylon covering said resilient layer.

* * * * *